United States Patent [19]
Depetris

[11] Patent Number: 4,911,051
[45] Date of Patent: Mar. 27, 1990

[54] CUTTING APPARATUS FOR OSTOMY SKIN BARRIER

[76] Inventor: Peter Depetris, P.O. Box 906, Niagara Falls, N.Y. 14302

[21] Appl. No.: 335,803

[22] Filed: Apr. 10, 1989

[51] Int. Cl.$^4$ ............................................. B26D 1/02
[52] U.S. Cl. .......................................... 83/856; 30/310
[58] Field of Search .................. 30/300, 310; 83/856, 83/574

[56] References Cited

U.S. PATENT DOCUMENTS

| | | | |
|---|---|---|---|
| 2,691,823 | 10/1954 | Dombrowski | 30/300 |
| 2,735,486 | 2/1956 | Millard | 30/310 |
| 4,060,893 | 12/1977 | Matsuura | 30/310 |
| 4,173,913 | 11/1979 | Nicholson | 30/564 |
| 4,548,118 | 10/1985 | Brosch | 30/310 |
| 4,581,824 | 4/1986 | Wilkins et al. | 30/310 |

Primary Examiner—Frank T. Yost
Assistant Examiner—Scott A. Smith
Attorney, Agent, or Firm—Harness, Dickey & Pierce

[57] ABSTRACT

An apparatus for cutting an interior opening in a sheet of material, such as an ostomy skin barrier, has a base with a flat cutting surface and a spindle extending out of the cutting surface. The spindle has a slot in its top which holds an arm having a cutting blade affixed thereto. The blade extends down to the cutting surface and remains stationary during cutting operations. Cutting is performed by rotating the sheet being cut about the spindle.

8 Claims, 4 Drawing Sheets

CUTTING APPARATUS FOR OSTOMY SKIN BARRIER

BACKGROUND OF THE INVENTION

Technical Field

A cutting apparatus, and more particularly, an apparatus for cutting an interior opening in a sheet of material.

Background Information

When an excretory organ in the human body becomes diseased or otherwise malfunctions, it may be necessary to remove or bypass the organ by means of a surgical procedure, such as a colostomy, ileostomy, or urostomy. Once the organ has been removed or bypassed, it is necessary to provide an artificial orifice in the skin termed a "stoma" to excrete waste from the body which would otherwise have passed through that organ.

A number of ostomy waste collection systems are known in the art for collecting wast excreted from the body via the stoma in a hygienic manner. An example of an ostomy system of this type is manufactured by Hollister, Inc., 2000 Hollister Drive, Libertyville, Ill. 60048, U.S.A.

The typical system comprises two components, an ostomy bag which accumulates the waste and a skin barrier which adheres to the skin around the stoma and provides a means for maintaining the ostomy bag in fluid communication with the stoma. The skin barrier also protects the skin around the stoma from undesirable contact with the waste exiting the stoma.

The skin barrier is fabricated from an elastic gummy material which enables it to conform and adhere to the skin with minimal discomfort to the wearer and which prevents it from absorbing substantial amounts of waste. The skin barrier has an adhesive backing for adherence to the body, although a sheet of paper is placed over the adhesive backing to preserve it during handling. The paper is removed from the surface when it is desired to attach the barrier to the skin of the user.

Both the skin barrier and ostomy bag are equipped with flanges which act as coupling and fluid communication elements for the two components. In order for the system to perform according to its intended function, it is necessary to provide the skin barrier with a central opening concentric to the flange of the barrier. This opening must correspond as closely as possible to the size and shape of the stoma. If the opening is too big, the peristomal skin is subjected to irritation caused by exposure to waste. If the opening is too small, the opening can block the passage of waste through the stoma.

Unfortunately, it is virtually impossible to precut a standard opening in all skin barriers which will have utility to every user because the size and shape of each individual stoma can vary greatly. In the majority of cases, the stoma is circular, but in the remaining cases, the stoma may have an irregular shape. Furthermore, the size and shape of each stoma usually changes over time.

Thus, each user must cut the central opening in their skin barrier to conform to the dimensions of their particular stoma. The user can cut the opening in the skin barrier with a conventional scissors or knife. However, it is very difficult to produce an accurate cut with one of these implements because of the gumminess and elasticity of the barriers. Accurately cutting the barriers requires greater dexterity than many aged users of ostomy systems possess.

For these reasons, specialized tools have been developed which enable one to cut circular openings in ostomy skin barriers. Examples of such tools are disclosed in U.S. Pat. Nos. 4,173,913 to Nicholson and 4,548,118 to Brosch.

The tools disclosed in both of these patents operate by placing a skin barrier in a holder which fits around the skin barrier. A blade and blade guide are coupled with the holder. The operator traces the blade around the circumference of the desired opening in the skin barrier, thereby cutting out the opening.

The disclosed tools have a number of disadvantages. Since the blade moves across the surface of the stationary holder, using it as a cutting surface, the blade undergoes considerable wear with each use. Furthermore, the tools can be relatively large and cumbersome because they must be large enough to enclose the entire skin barrier they are cutting. Finally, although the position of the blade in the tool is adjustable, adjustment of the blade position requires more than minimal dexterity by the user.

In view of the shortcomings of existing tools known in the art, a need exists for a compact tool which effectively cuts openings in a sheet of material, such as a skin barrier of an ostomy system. A need exists for a cutting tool which is readily adjustable for cutting openings of different sizes. A need exists for a tool which is easy to use with two hands and which requires minimal dexterity. A need exists for a cutting tool which has few moving parts, thereby reducing its cost of manufacture. Finally, a need exists for a cutting tool which minimizes blade wear to enhance the life of the blade and reduce the frequency of blade replacement.

SUMMARY OF THE INVENTION

The present invention is an apparatus generally suitable for cutting an opening in a sheet of material. The apparatus is particularly suitable for cutting a circular or irregular opening in the interior of an ostomy skin barrier, wherein the opening corresponds to the size and shape of a stoma.

The apparatus of the present invention comprises a base having a flat cutting surface and a spindle extending perpendicularly from a central portion of the cutting surface. The spindle has a slot in its top which accepts and holds an arm in a stationary position relative to the spindle and base. A blade is affixed to the arm, such that it is positioned adjacent the cutting surface a spatial distance away from the spindle when the arm is in the slot.

This spatial distance is adjustable to different predetermined intervals by means of a cooperative interlocking system. The system comprises a series of uniformly sized grooves in the slot which accept teeth correspondingly formed in the arm in the manner of a tongue and groove joint. Once the arm is positioned in the slot, the blade is laterally fixed relative to the spindle and cutting surface. However, if it is desired to change the spatial distance between the blade and the spindle, the arm can be vertically withdrawn from the slot and the teeth can be realigned with the grooves such that the blade is either further or closer to the spindle than before.

The apparatus of the present invention is operated by removing the arm from the slot. A sheet of material desired to be cut is placed over the spindle flush against the cutting surface. Placement of the sheet over the spindle is facilitated if a pre-cut opening exists in the sheet corresponding exactly to the size of the spindle cross section.

The arm is then replaced in the slot of the spindle, aligning the teeth and grooves such that the blade contacts the sheet at a point on the circumference of the anticipated opening. The user applies pressure to the arm where it joins the spindle so that the blade penetrates the sheet to the desired depth. The sheet is then rotated about the spindle so that the blade tracks a continuous cut through the sheet around the entire circumference of the desired opening. After cutting, the arm is removed from the slot and the sheet is removed from the spindle.

The present invention has a number of advantages over cutting tools known in the art. The apparatus of the present invention does not hold the sheet and cutting surface stationary while rotating the blade about the spindle during the cutting operation. As a result, the breadth of the present apparatus can be much less than the sheet being cut. In addition, because only the sheet rotates while the cutting surface and blade remain stationary relative to one another during cutting, blade wear is reduced which extends the lifetime of the blade.

The tongue-and-groove joint between the arm and the spindle enables rapid and easy adjustment of the blade position to a number of predetermined positions. This enables one to use the present apparatus to cut a number of different sized openings in a given sheet. The joint also enables one to position the blade such that it cuts only to a desired depth in the sheet. Thus, for example, one can cut through the gummy material of a skin barrier without cutting the paper backing. This prevents unnecessary dulling of the blade by the paper, which further adds to the lifetime of the blade.

DESCRIPTION OF PREFERRED EMBODIMENTS

Figure 1:
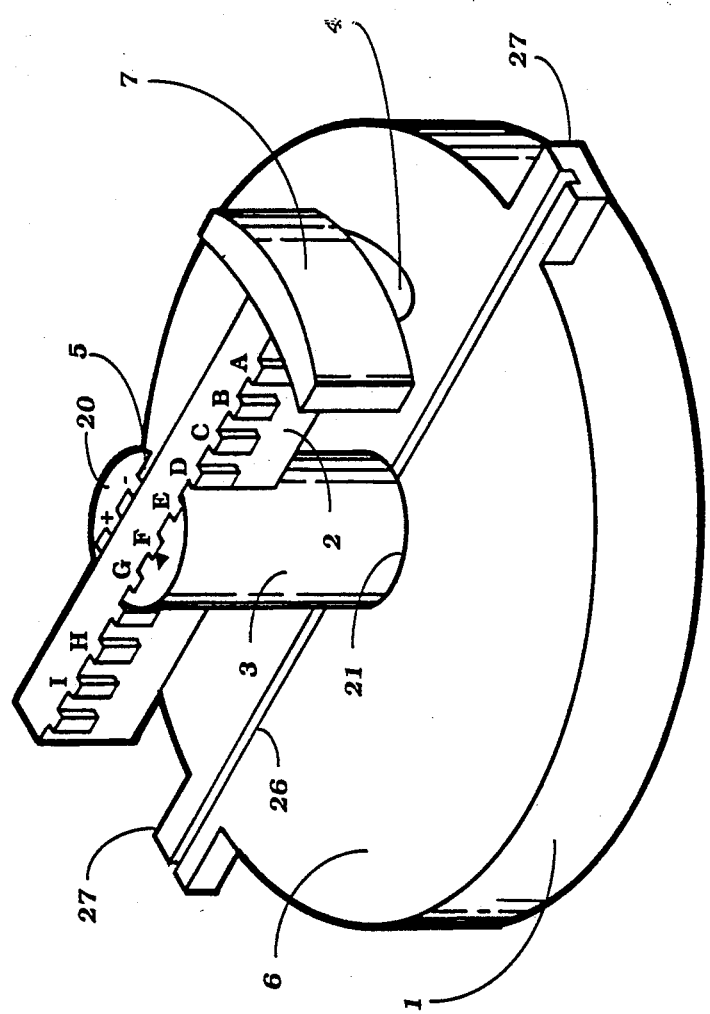
FIG. 1 is a perspective view of the cutting apparatus of the present invention.

The present embodiment of the invention is described with reference to the structure shown in FIGS. 1–3. FIG. 1 shows the apparatus having base 1 with flat cutting surface 6. Central spindle 3 is fixably attached at one end 21 to base 1 in a perpendicular orientation to cutting surface 6. Spindle 3 has longitudinal slot 5 formed through the diameter of spindle 3 at end 20 of spindle 3 opposite cutting surface 6.

Arm 2 is positioned in slot 5 of spindle 3 by means of the tongue-and-groove joint such that arm 2 is substantially free to move vertically upward relative to cutting surface 6, but cannot move horizontally relative thereto. Blade 4 is affixed to bottom of arm head 7 at the opposite end of arm 2 from spindle 3. As shown in FIG. 3, blade 4 is adjacent cutting surface 6 in its normal resting position and blade 4 is aligned in a vertical orientation to cutting surface 6.

Blade 4 is preferably made of a material which will maintain a sharp edge after several cuttings. Although the present invention is not limited to any particular blade shape or material, a razor-like semi-circular blade made of a hardened steel or other metal is preferred. Since blade 4 does not move relative to cutting surface 6 in the present embodiment, base 1 can be fabricated of any lightweight, inexpensive material such as molded rigid plastic.

As shown in FIG. 1, spindle 3 and base 1 are molded from plastic in a single unit and arm 2 and head 7 are molded from plastic as a separate single unit. Blade 4 is affixed to head 7 in any manner known to one of ordinary skill in the art.

Figure 2:
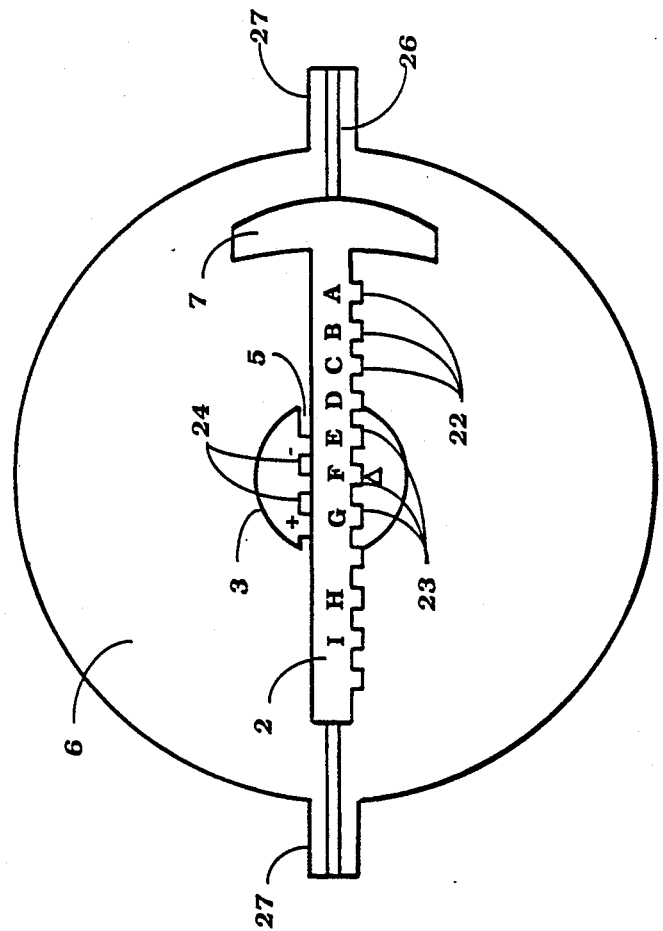
FIG. 2 is a top view of the cutting apparatus.

The tongue-and-groove joint of the present invention is shown in greater detail in FIG. 2. Teeth or tongues 22 are provided on one side of arm 2 which fit into grooves 23 in the side of slot 5. Reference letters, as shown here, or any other markings may be provided to assist the user in positioning arm 2 such that blade 4 tracks a cut to create an opening of a desired size in a sheet. For example, if A is aligned opposite an arrow on the spindle 3 adjacent to slot 23, this setting could cause the apparatus to cut a 1 inch diameter opening; alignment of B with the arrow could create a 1.25 diameter inch opening; alignment of C with the arrow could create a 1.5 diameter inch opening, and so on.

An additional set of grooves 24 can be provided in the opposite side of slot 5 from the arrow which have an exact opposite pattern from the first set of grooves 23. By turning arm 2 around and fitting teeth 22 into grooves 24, one can more finely adjust the opening size in the sheet to, for example, $\frac{1}{8}$ inch diameter increments. Thus, if one desires to cut an opening having a diameter $\frac{1}{8}$ inch smaller than the opening corresponding to C, one simply turns arm 2 around and aligns the reference C on arm 2 with the reference "−" on spindle 3. If one wishes to cut an opening having a diameter $\frac{1}{8}$ inch larger than the opening corresponding to C, one would align C with the reference "+".

Although the grooves 23 and 24 and teeth 22 are shown as having right angles, other geometries are possible. For example, grooves 23 and 24 may be v-shaped with teeth 22 correspondingly shaped to fit in the v-shaped grooves.

The embodiment of FIG. 1 is operated by removing arm 2 from slot 5. A sheet to be cut is placed over spindle 3 onto cutting surface 6. Arm 2 is then replaced in slot 5 at a desired position. Pressure is applied to arm 2 at the center of the joint between arm 2 and spindle 5, such that blade 4 penetrates the sheet. The sheet is rotated about spindle 5 until a continuous uniform circular cut is formed in the sheet.

One can also use the present apparatus to cut an irregular shape in a sheet. One first traces the shape of the desired opening to be cut on the surface of the sheet. One then selects a distance from blade 4 to spindle 3 which is less than or equal to the nearest point on the traced shape to spindle 3. A circle is cut out of the sheet having a circumference defined by this point. Thereafter, one moves the sheet horizontally across cutting surface 6 in accordance with the irregular shape while rotating the sheet until cutting of the opening is complete.

Figure 3:
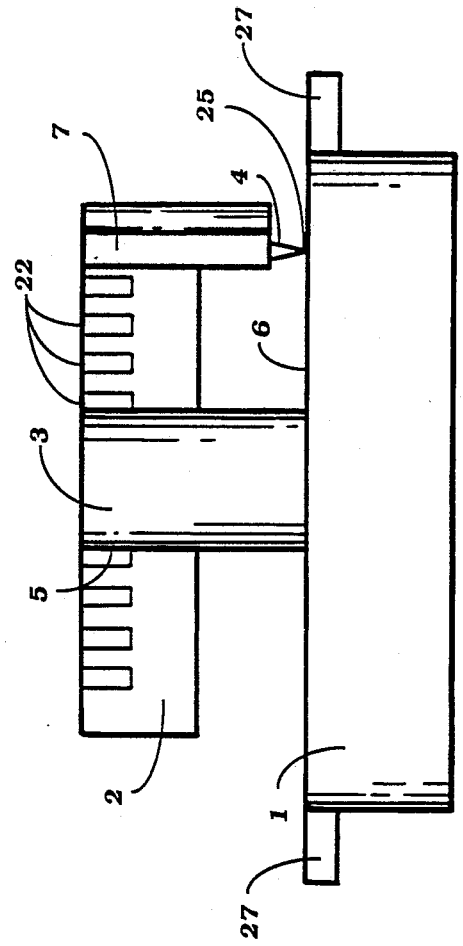
FIG. 3 is a side view of the cutting apparatus.

According to the embodiment of the invention shown in FIG. 3, the dimensions of slot 5, blade 4 and arm 2 are determined such that blade 4 is adjacent to, but does not contact, cutting surface 6 when arm 2 is resting in slot 5. A small gap 25 is provided between blade 4 and cutting surface 6, such that when cutting an ostomy skin barrier, blade 4 cuts through the gummy material of the barrier, but does not cut through the paper backing of the barrier.

This capability can be facilitated by providing a shallow groove 26 in cutting surface 6 which is in line with slot 5 and runs perpendicular to the longitudinal axis of spindle 3. Groove 26 provides a void in cutting surface 6 immediately below the point where the blade 4 contacts the sheet and prevents blade 4 from penetrating all the way through the bottom surface of the sheet.

If one desires blade 4 to penetrate all the way through the sheet down to cutting surface 6 using the embodiment of FIG. 3, one can shift the pressure being applied on arm 2 from the center of the joint to the edge of the joint nearest blade 4. This pressure drives blade 4 downward completely through the sheet.

Conversely, if one desires to form a shallower cut in the sheet, one can shift the pressure applied to the arm from the center of the joint back toward the edge of the joint furthest from blade 4.

When very large sheets are being cut, cutting surface 6 may further be provided with one or more extensions 27 at the outer edge of cutting surface 6 to support the larger sheets without substantially increasing the size or weight of the apparatus.

The utility of the present apparatus as shown in FIG. 1 is illustrated by the following example. However, the example is not to be construed as limiting the scope of the invention.

EXAMPLE

A skin barrier manufactured by Hollister, Inc. has outside dimensions of 4 inches square. The flange of the skin barrier has an inside diameter of 3 inches. The barrier has a central precut opening which is concentric to the flange and has a diameter of ½ inch. The side of the barrier opposite the flange has an adhesive backing which is covered with protective paper.

The barrier is made up of a gummy elastic material which is 1/16 inch thick. The paper backing is 1/128 inch thick. The barrier is placed on the cutting surface of the present invention by sliding the precut opening over the spindle which has substantially the same diameter as the precut opening.

A uniform circular opening concentric to the flange having a diameter of 1.5 inches is desired in the barrier. Therefore, the arm is placed in the slot of the spindle such that the reference D on the arm aligns with the arrow on the spindle. This alignment corresponds to a blade distance of ¾ inch from the center of the spindle.

The barrier is rotated about the spindle while holding the arm in the slot by applying pressure to the arm at the center of the joint between the spindle and the arm. The barrier is rotated until a continuous cut exists in the barrier. The arm is then removed from the slot and the barrier is removed from the spindle. The inner section of the barrier, which has been cut out, is peeled away from the paper and disposed. The barrier is now ready for application to the skin of a user having a circular stoma with a diameter of 1.5 inches.

Figure 4:
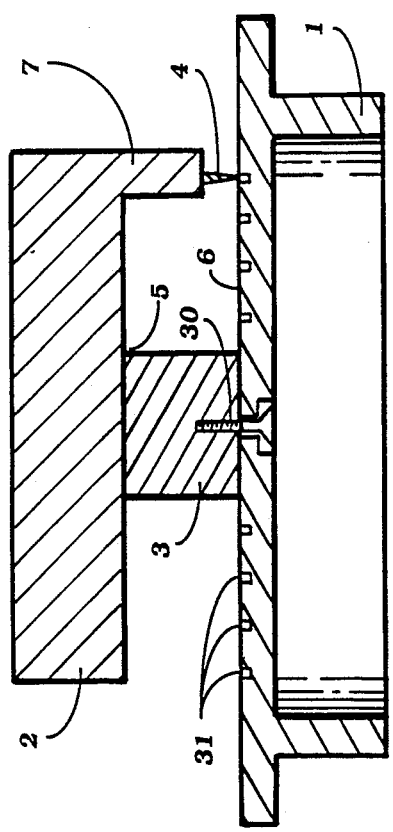
FIG. 4 is a cut-away view of a second embodiment of the cutting apparatus of the present invention.

A separate embodiment of the present invention is shown in FIG. 4. The apparatus of FIG. 1 is modified such that blade 4', arm 2' and spindle 3' all rotate relative to cutting surface 6' and base 1' of the apparatus. Although this embodiment is less preferred because it negates many of the above-recited advantages of the present invention, it has utility where the sheet of material being cut is so gummy that it sticks to spindle 3'. If this occurs, the precut central opening in the sheet becomes distorted when the sheet is rotated about spindle 3'.

The alternative embodiment of FIG. 4 alleviates this problem by rotably mounting spindle 3' on base 1' by means of pin 30 in a manner within the purview of one of ordinary skill in the art. Instead of a perpendicular groove 26 in cutting surface 6', circular groove 31 can be placed in cutting surface 6' which are concentric to spindle 3' and are aligned with the predetermined settings of blade 4'. Thus, grooves 31 will follow the cutting track of blade 4' as it rotates around cutting surface 6'. In all other respects, the embodiment of FIG. 4 is identical to the embodiment of FIG. 1, including the tongue-and-groove system of joining arm 2' and spindle 3'.

While the foregoing embodiments of the invention have been described and shown, it is understood that alternatives and modifications, such as those suggested and others, may be made thereto and fall within the scope of the present invention.

I claim:

1. An apparatus for cutting a sheet of material comprising:
   (a) a base having a substantially flat cutting surface;
   (b) a spindle fixably attached to said base in a substantially centralized perpendicular orientation to said cutting surface;
   (c) an arm positioned on said spindle and extending away from the longitudinal axis of said spindle; and
   (d) a blade attached to said arm a spatial distance from said spindle and positioned adjacent said cutting surface, said blade substantially fixed to prevent rotational or lateral movement relative to said cutting surface.

2. The apparatus of claim 1, wherein said arm is removably positioned in a longitudinal slot formed in said spindle.

3. The apparatus of claim 2, wherein said slot has a plurality of grooves formed therein and said arm has a plurality of teeth formed thereon, said grooves capable of accepting said teeth when said arm is positioned in said slot to form a joint substantially fixing said arm to prevent rotational or lateral movement relative to said cutting surface.

4. The apparatus of claim 3 wherein said grooves and said teeth are formed at uniform predetermined intervals to define a series of spatial distances between said blade and said spindle.

5. The apparatus of claim 4, wherein said arm is removably positioned in said slot at any one of said spatial distances.

6. The apparatus of claim 1, wherein said cutting surface has a groove formed therein, said groove aligned beneath said blade and extending perpendicularly relative to the longitudinal axis of said spindle.

7. The apparatus of claim 1, wherein said blade is positioned adjacent to and slightly above said cutting surface.

8. The apparatus of claim 1, wherein said blade is positioned in a vertical orientation to said cutting surface.

* * * * *